(12) United States Patent
Raghuraman et al.

(10) Patent No.: US 7,637,151 B2
(45) Date of Patent: Dec. 29, 2009

(54) ENHANCED DOWNHOLE FLUID ANALYSIS

(75) Inventors: Bhavani Raghuraman, Lexington, MA (US); Kristofer Gunnar Paso, Brooklyn Park, MN (US); Neil William Bostrom, Cambridge, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 263 days.

(21) Appl. No.: 11/612,596

(22) Filed: Dec. 19, 2006

(65) Prior Publication Data

US 2008/0141767 A1 Jun. 19, 2008

(51) Int. Cl.
*E21B 47/08* (2006.01)
(52) U.S. Cl. .................. 73/152.55; 73/863; 250/255
(58) Field of Classification Search ............... 73/152.55, 73/863, 152.01, 152.54; 250/255, 256, 343
See application file for complete search history.

(56) References Cited

U.S. PATENT DOCUMENTS

| | | | | |
|---|---|---|---|---|
| 4,739,654 | A * | 4/1988 | Pilkington et al. | 73/152.24 |
| 5,859,430 | A * | 1/1999 | Mullins et al. | 250/255 |
| 5,939,717 | A | 8/1999 | Mullins | |
| 6,670,605 | B1 * | 12/2003 | Storm et al. | 250/255 |
| 7,231,819 | B2 * | 6/2007 | Jones et al. | 73/152.23 |
| 7,435,597 | B2 * | 10/2008 | Mango | 436/31 |
| 2004/0045350 | A1 * | 3/2004 | Jones et al. | 73/152.23 |
| 2006/0106993 | A1 | 5/2006 | Khare et al. | |

FOREIGN PATENT DOCUMENTS

| | | |
|---|---|---|
| EP | 0508595 A1 | 10/1992 |
| EP | 1862781 A1 | 5/2006 |
| EP | 1686238 A1 | 8/2006 |
| WO | 0173424 A1 | 10/2001 |
| WO | 2002/077613 A2 | 10/2002 |
| WO | 2006/094694 A1 | 9/2006 |

OTHER PUBLICATIONS

Andrews et al., "Quantifying Contamination Using Color of Crude and Condensate", Oilfield Review, Autumn 2001, pp. 24-43.
Betancourt et al., "Analyzing Hydrocarbons in the Borehole", Oilfield Review, Autumn 2003, pp. 54-61.
Betancourt et al., "Exploration Applications of Downhole Measurement of Crude Oil Composition and Fluorescence", SPE 87011, 2004.

(Continued)

*Primary Examiner*—Hezron Williams
*Assistant Examiner*—Rodney T Frank
(74) *Attorney, Agent, or Firm*—James M. McAleenan; Jody Lynn DeStefanis; Dale Gaudier

(57) ABSTRACT

The operation, analysis and interpretation of a chromatographic system can be significantly enhanced by coupling therewith one or more fluid property measurements that provides an initial indication of the fluid type, the presence of any contamination, an estimate of the hydrocarbon composition (C1, C2-C5 and C6+), gas/oil ratio, color and/or fluorescence measurements. Other measurements that can be used in the initial stage can include density, viscosity, phase transition determinations. These measurements may be used to enhance, in real-time, the GC sampling protocol, the analysis protocol and also improve the robustness of the interpretation of the chromatogram.

20 Claims, 6 Drawing Sheets

OTHER PUBLICATIONS

Ahmed, "Comparative Study of Eight Equations of State for Predicting Hydrocarbon Volumetric Phase Behavior", SPE 15673 Reservoir Engineering, Feb. 1988, pp. 337-348.

Lo et al., "Mixing Rules and Correlations of NMR Relaxation Time with Viscosity, Diffusivity, and Gas/Oil Ratio of Methane/Hydrocarbon Mixtures", Mar. 2002 SPE 77264 Journal, pp. 24-34.

Fujisawa et al., "Large Hydrocarbon Compositional Gradient Revealed by In-Situ Optical Spectroscopy", SPE 89704, 2004.

ASTM International, "Standard Test Method for Determination of Boiling Range Distribution of Crude Petroleum by Gas Chromatography", Designation: D 5307-97 (Reapproved 2002).

ASTM International, "Standard Test Method for Analysis of Petroleum Waxes by Gas Chromatography", Designation: D 5442-93 (Reapproved 2003).

* cited by examiner

ENHANCED DOWNHOLE FLUID ANALYSIS

BACKGROUND OF THE INVENTION

1. Field of the Invention

The present invention relates to formation fluid analysis and, more particularly, to enhanced systems and method of chromatographic analysis of downhole fluids, for example, wellbore fluids, treatment fluids, formation fluids, and drilling muds, utilizing an initial characterization of a property of the fluid prior to further analysis.

2. Description of Related Art

Chromatographic analysis is a technique that is generally used to characterize subsurface produced hydrocarbons in surface based facilities. It provide high-resolution compositional analysis to long chain hydrocarbon compounds including, for example, C36+ or higher. The techniques can be used for equation of state tuning and subsequent compositional modeling of fluids in reservoirs to facilitate or provide reservoir production strategy and planning and design of surface based production facilities.

In surface-based laboratories, typically, the formation hydrocarbon sample is flashed to ambient conditions to separate dissolved gas and liquid hydrocarbon phases. Any water that may be present in the collected liquid hydrocarbon (oil) phase, is separated. Not only can an oil-water mixed injection interfere in quantitative hydrocarbon analysis, but exposure to water can also cause the stationary phase in the chromatography column to degrade rapidly. Standard analytical protocols that include column type and configurations, temperature programs, carrier gas flow rates and pressures, injector and detector temperatures are used for characterization. One or more chromatographic systems and protocols may be used for analysis of the gas and liquid hydrocarbon phase fractions to maximize resolution and accuracy. The typical analysis time of such standardized techniques is in the range of several minutes to an hour.

To access a formation fluid, a formation tester tool with a sampling probe, pump module and a flow line is commonly used. Typically, a sampling probe contacts the formation and a pump is used to withdraw fluid from the formation into a flow line that may contain one or more sensor trains for in situ analysis. Subsequent to that, the fluid may either be disposed into the wellbore or collected in sample bottles for further surface based analysis. The fluid may be single phase or a multiphase mixture of water and gas/liquid hydrocarbons. The initial fluid that is withdrawn into the tool is generally highly contaminated by drilling mud filtrate. This filtrate can be either water-based (immiscible with formation hydrocarbon) or oil-based (miscible with formation hydrocarbon). With continued pumping over time, the contamination drops and the fluid becomes more representative of the true formation fluid.

Pilkington, in U.S. Pat. No. 4,739,654, discloses a method and apparatus for downhole chromatography of single phase flows using a chromatographic system. In the art to Pilkington a resistivity sensor is used in identifying hydrocarbon samples which are not highly contaminated by oil based mud filtrate. Pilkington fails, however, to recite the use of alternative sensors, such as optical sensors, for tracking oil based mud contamination. Additionally, Pilkington fails to address the differentiation between formation water (or a water based mud filtrate) and oil.

If only a chromatographic analytical system is deployed in a downhole environment, the sampling would be blind, with no a priori knowledge of fluid type, e.g., water, gas, and/or liquid hydrocarbon or contamination. Sampling and injection of water into the chromatographic system should be avoided because it is not relevant for hydrocarbon pressure-volume-temperature (PVT) characterization. Water exposure may also cause rapid column stationary phase degradation and/or interference in the quantitative hydrocarbon analysis. Yet another problem with blind sampling is when the hydrocarbon fluid is a mixture of gas and liquid phase, as then it is difficult to sample both phases in representative fractions to get the accurate quantification. To maintain the integrity of the analysis, one would prefer to sample the two phases separately by single-phase injections and get their compositions independently.

Furthermore, it is important to know the percentage contamination, especially when the sample contains miscible oil-based mud filtrate, as high contamination drastically alters the properties of the formation fluid and hence the compositional analysis of such a sample has no value. Acceptable contamination levels in formation fluid samples are of the order of 5% or less for oil-based mud filtrates. With water-based mud filtrates, segregation of the hydrocarbon is important prior to analysis. It is thus advantageous that fluid property characterization and chromatography analysis be done only when contamination levels are below acceptable levels in order for the results to be used for equation of state (EOS) tuning and estimating fluid properties. While chromatography is generally used to estimate contamination in the surface laboratories, repeat sampling over long pumping times to track contamination by chromatography under downhole conditions is not efficient. Not only does it increase consumption of finite resources on the downhole tool, such as carrier gas, it can also cause degradation of column performance. Most columns are reconditioned after a certain number of injections. If more efficient methods are available for contamination tracking, it is advantageous to use chromatography only for sample analysis.

A wellbore typically intersects several formation layers filled with various types of fluid ranging from dry gas to heavy oil. Thus the downhole tool should preferably be able to analyze various kinds of fluids in a single logging run. Without any a priori knowledge of the hydrocarbon sample type, one would have to go with a standard protocol for example, irrespective of whether it is dry gas, with components predominantly to C7 or a black oil, with components all the way to C36 and higher. Thus there is no possibility of tuning and optimizing it for the sample type to improve resolution and accuracy. This could also result in unnecessarily longer analysis times. Long wait times at an analysis station not only translates to higher costs related with rig time but also increases the risk of tool sticking in the wellbore. Longer analysis times would also mean increasing the consumables such as carrier gas, which is an important consideration in a downhole environment, as only limited supplies exist.

It is an aspect of the present invention to address these deficiencies in the prior art.

SUMMARY OF THE INVENTION

In accordance with some aspects, the invention is directed to an analytical system comprising a primary stage disposed to receive at least a portion of an analyte and provide an indication of at least one property of the fluid, and a secondary characterization stage disposed to receive at least a portion of the formation fluid and comprising at least one chromatographic analytical train. As used herein the terms "chromatographic analytical train", "analytical train" or "train" may include one or more sampler/injectors, one or more columns, and one or more detectors fluidly connected to provide a relative characterization of the eluent from the one or more columns. Additionally, for the purpose of clarity, the term "analyte" is herein used to refer to a fluid sample that is undergoing analysis. In accordance with the present invention, the analyte may be single phase or multiphase and may include a liquid hydrocarbon phase, a water phase, or a gaseous hydrocarbon phase.

In accordance with one or more aspects, the invention is directed to a method of characterizing an analyte. The method can comprise one or more acts of determining at least one first property of the analyte in the first characterization stage and determining the composition of at least a portion of the analyte in a second characterization stage based at least partially on the at least one first property.

DETAILED DESCRIPTION OF THE INVENTION

Figure 1:
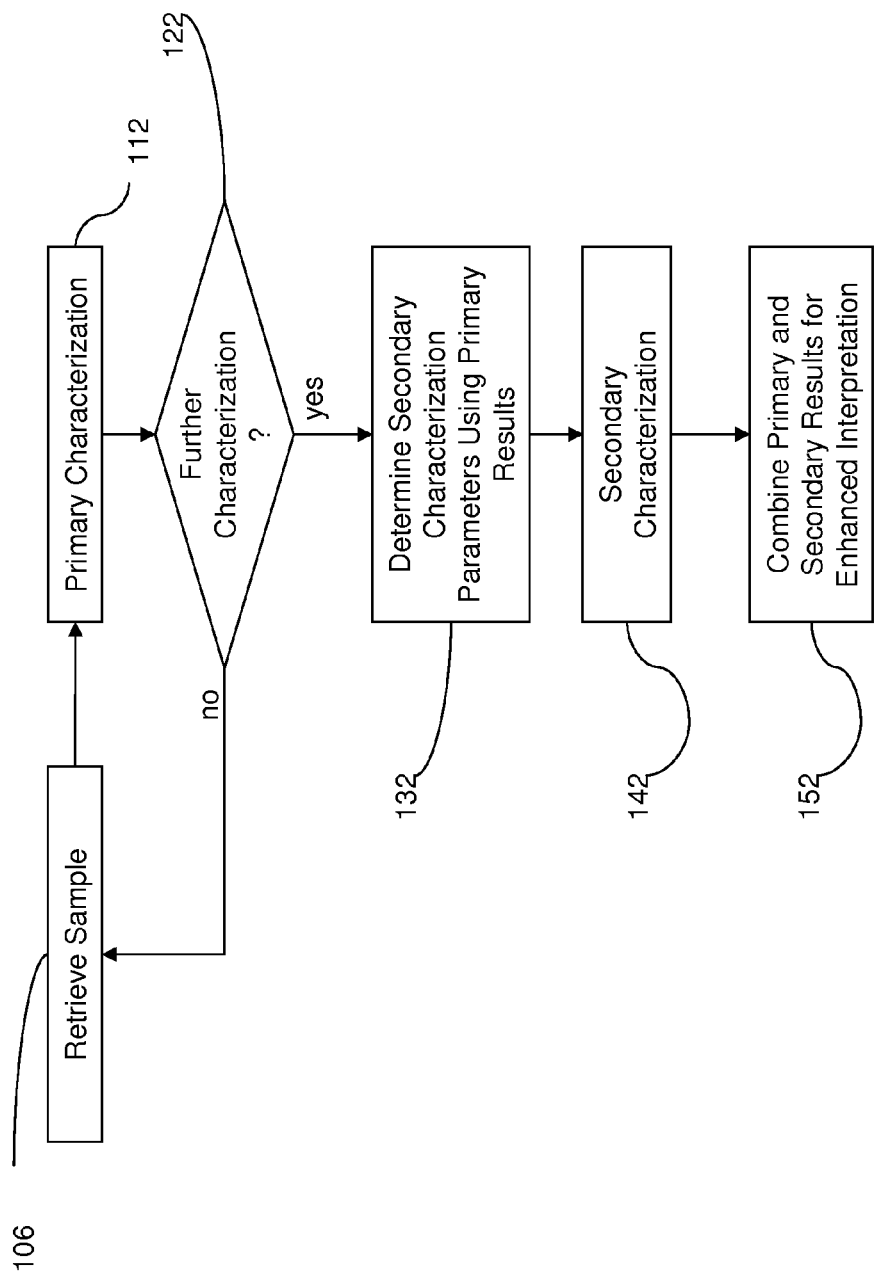
FIG. 1 illustrates a flowchart in accordance with one or more embodiments of the invention.

The invention provides systems and techniques of downhole, in-situ, formation fluid characterization. Some aspects of the invention provide systems and techniques that facilitate chromatographic characterization of formation fluids. Facilitating such characterization of formation fluids in downhole environments can involve initially determining at least one or more properties of the formation fluid, such as optical signature, fluid type, fluid density, fluid color, fluid fluorescence gas-oil ratio and low resolution composition. Thus, some aspects of the invention relate to tiered or staged characterization systems and techniques wherein a first analytical step or stage can be utilized with one or more further analytical stages to characterize the nature of the formation fluid. The first characterization stage can involve a non-destructive stage including, for example, techniques that measure an intrinsic property of a fluid to be analyzed. The fluid may be a formation fluid, and the intrinsic property may be at least one fluid property of a component of the formation fluid. One skilled in the art will recognize that numerous alternative fluids may be used in practicing the present invention. Furthermore, for illustrative purposes, the present invention will be described in relation to a fluid encountered in a downhole environment, herein referred to as a "formation fluid". Such an illustration is not intended to be limiting in scope, as the present invention may be practiced on a variety of alternative fluids, as understood by one skilled in the art. The first or initial characterization function can facilitate or accelerate characterization of the formation fluid, or at least a portion thereof. However, a first stage that performs destructive characterization of a fraction of the sample may also be utilized to provide an initial characterization if for example the first stage characterization is done in a bypass setup.

Further features of the invention are directed to downhole analysis involving rapid and efficient characterization while achieving the required chromatographic separation. For example, the invention can allow choice of optimum chromatographic separation protocol based on the knowledge of the type of fluid. However, with no a priori knowledge of the fluid, a single protocol would be used to ensure proper characterization. This may unnecessarily prolong the analytical cycle or require an unnecessarily complex protocol. For example, if the sample predominantly comprises dry gas, unnecessarily long analysis times and temperature heating ramps to go to high column temperatures primarily targeting non-present higher carbon number components would be utilized. This could also result in longer cooling times for the system before the next analysis is performed.

To use the gas chromatography output for EOS tuning, the mass or mole fractions of all the components in the sample fluid should be known. In surface-based laboratories, the quantification of the chromatogram in terms of mole fraction or mass fraction requires accounting for the components that are present in the sample but not in the chromatogram output. This could be because (i) they were too strongly adsorbed to the stationary phase and never eluted during the analysis time, (ii) never vaporized in the sampler/injector because of low volatility at the temperature and pressure conditions employed, and hence not part of the vaporized sample plug injected into the column, or (iii) they were backflushed and so did not pass through the detector. In the surface-based analyses, these components are generally accounted for by using internal standards (specific components that are mixed with the sample in a precisely measured proportion) such as in methods described in ASTM D5307-97 and D5442-93. Mixing internal standards with hydrocarbon samples with extreme precision in a downhole gas chromatographic tool, however, may be complicated and involved.

Some aspects of the invention can involve downhole tools or systems comprising one or more initial characterization systems, subsystems or components, which provide an initial value or nature of the fluid. The invention advantageously integrates chromatographic systems and techniques with other sensors and/or protocols such as those that are based on optical techniques, resistivity, NMR and/or provide intrinsic property measurements such as density and/or viscosity.

FIG. 1 exemplarily illustrates an embodiment of the invention. Optically-based subsystems can initially determine the presence of any aqueous phase or gas or liquid (oil) hydrocarbon phases in the analyte. Thus, the presence, or absence of water, oil and/or gas can be initially characterized in a primary characterization step 112. Further embodiments can, in some cases, provide at least an estimate of a ratio of any dissolved gas to oil (GOR) of the analyte. Some further aspects can involve color and fluorescence characterization of at least a portion or component of the analyte which can be further utilized in one or more subsequent or accompanying characterization trains. For example, the color and/or fluorescence of the liquid hydrocarbon phase can be determined and the determined initial or primary properties can provide a qualitative estimate of the nature of the oil, e.g., a light or heavy hydrocarbon oils. Absorption spectra in the visible to near-infra red region can be used to make a low-resolution compositional analysis, e.g., C1, C2-C5, or C6+, as well as any oil based mud contamination as recited in Andrews et al., "Quantifying Contamination Using Color of Crude and Condensate," Oilfield Review, Autumn 2001, pp. 24-43 and Betancourt et al., "Analyzing Hyrdocarbons in the Borehole," Oilfield Review, Autumn 2003, pp. 54-61 which describe these optical measurements in more detail. Further characterization, if appropriate, can be evaluated in step 122. If the sample is considered as contaminated or considered to primarily be comprised of undesirable components, no further characterization is considered and another sample can be retrieved, 122, no. Further, if the initial or primary characterization results are inconclusive, indeterminate and/or otherwise invalid, another sample can be retrieved. For illustrative purposes, this is denoted in step 106, yet one skilled in the art will recognize that the retrieval of another sample can occur at a variety of alternative stages, included at step 112 or 122. For example, if the retrieved analyte is comprised primarily of non-hydrocarbon components, the sample may be discarded and no further characterization will be performed. If a valid sample is considered for further evaluation, 122, yes, then the sample is transferred for secondary or subsequent analysis in one or more secondary characterization steps 142. In some cases, one or more optional steps of determining one or more parameters of the secondary characterization steps 132, e.g., in one or more chromatographic trains, can be performed based, at least partially, on the primary characterization results. Additional optional operations can involve combining the primary and secondary results 152 to provide an enhanced interpretation of the quality, character, and/or nature of the analyte.

In some embodiments of the invention, the hue and intensity of light transmitted or reflected from a sample can be utilized to distinguish oils of different composition. The light absorbed or optical density (OD), which can be a ratio of the incident light to transmitted light such that darker fluids have higher OD, can be used to provide a characterization of the components. For example, light hydrocarbons are typically colorless and do not absorb light in the visible spectrum whereas condensates can be clear or lightly shaded reddish-yellow tan because they absorb blue and heavy crude oil with complex molecules are typically dark brown because light throughout the visible spectrum is absorbed. Thus, in some embodiments of the invention, the first characterization stage comprises measuring optical density to provide an initial characterization of the sample. In some cases, the characteristics considered can be the presence of one or more fluid phases. Optical system based tools such as the Live Fluid Analyzer (LFA™) and Composition Fluid Analyzer or CFA™ from Schlumberger can also be used to detect single phase and multiphase flow, and further provide an indication of suitable sampling conditions or whether the retrieved sample should be further analyzed. In further embodiments of the invention, optics based systems as well as those that measure, for example, resistivity or conductivity of the fluid and those utilizing nuclear magnetic resonance (NMR) may be utilized in the first characterization stage.

Figure 2:
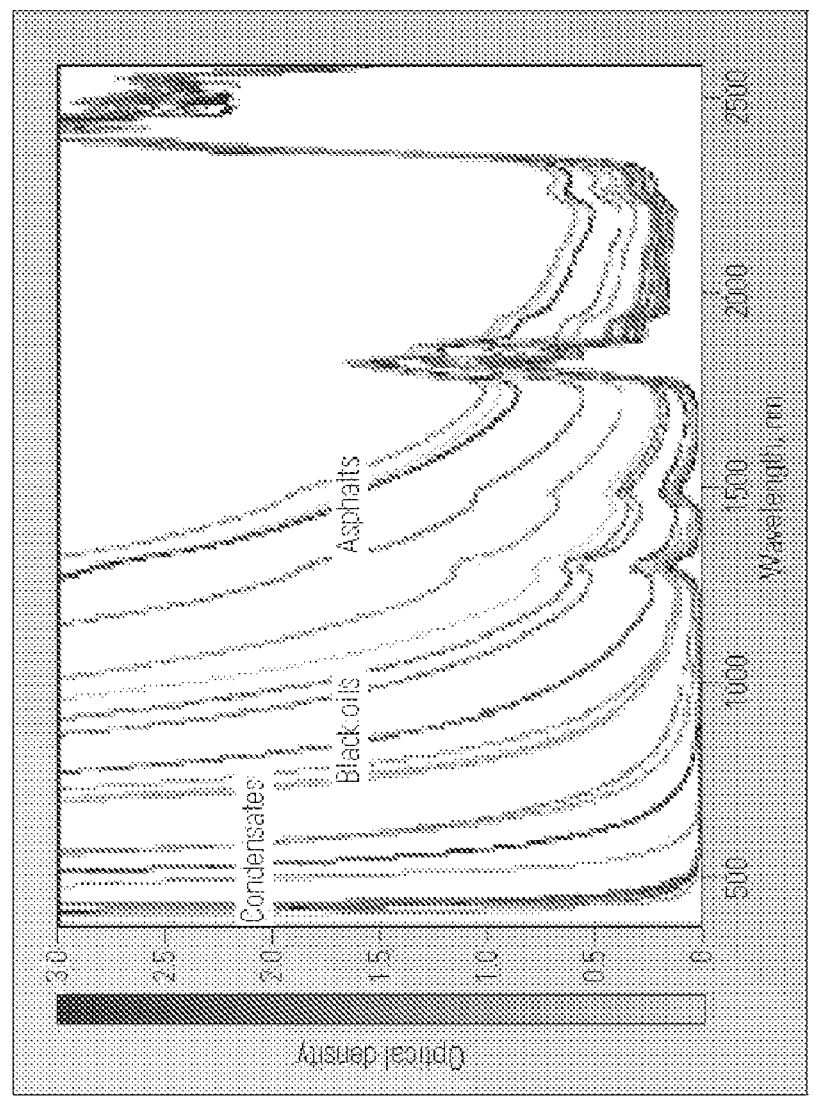
FIG. 2 is a chart showing the optical density of various oils as a function of wavelength.
Figure 3:
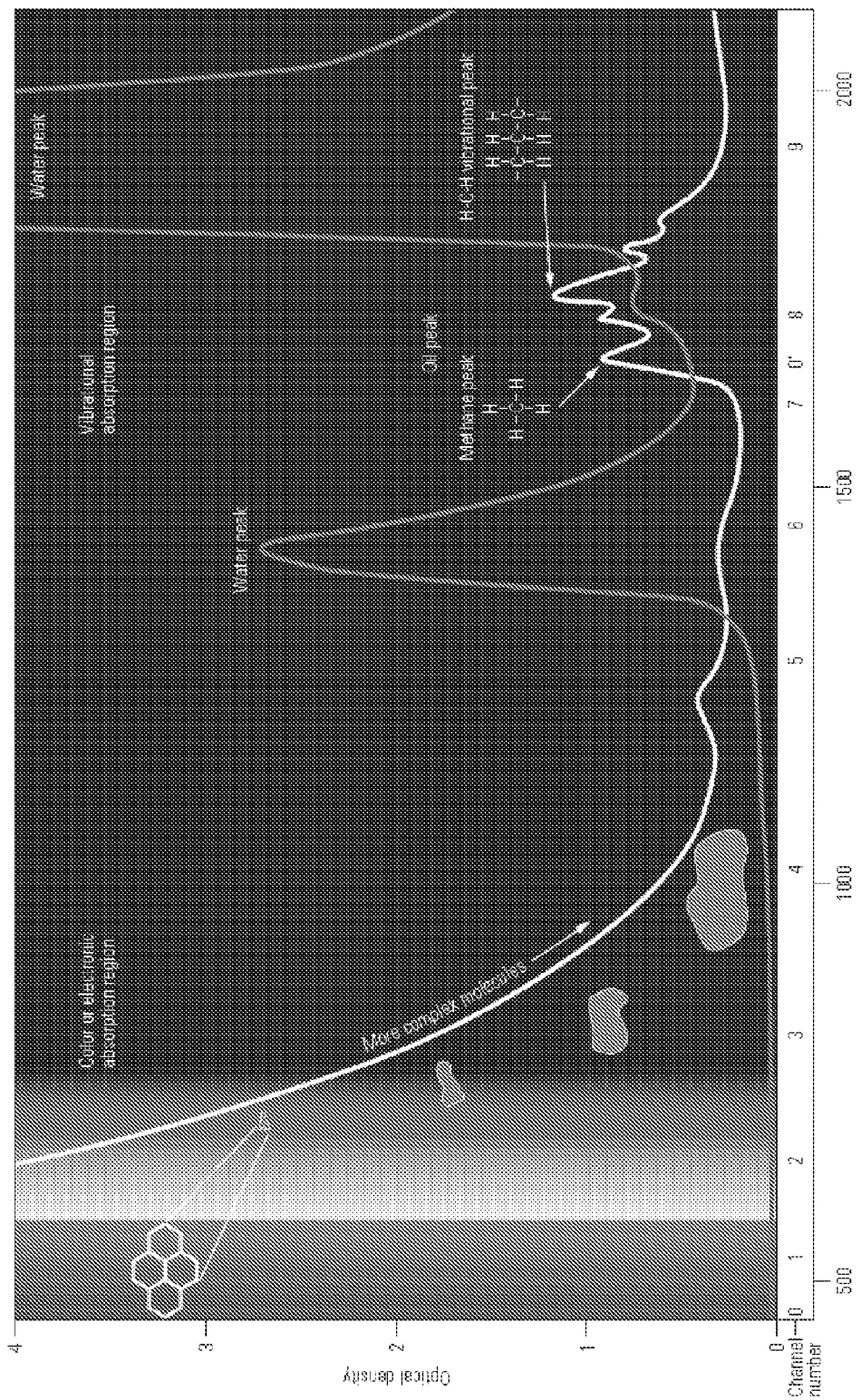
FIG. 3 is a chart showing the absorption spectrum of an oil sample and a water sample.

Particularly advantageous embodiments of the invention can utilize spectral measurements on a sample to provide the initial characteristic or a plurality of initial characteristics. In some particular cases, a spectral signal from a sample can be captured and particular components of the spectrum, e.g., light at selective wavelengths can provide an indication or absence of a desirable and/or an undesirable component in the sample. FIGS. 2 and 3 (based upon data contained in Andrews et al., "Quantifying Contamination Using Color of Crude and Condensate," Oilfield Review, Autumn 2001, pp. 24-43), exemplarily shows a chart of the relationship between optical density and wavelength of light. As shown in FIG. 3, water typically absorbs light at near-infrared wavelengths, about 1445 and 1930 nanometers. Thus, the presence of water in a sample can be determined using optical techniques by capturing/observing a response or characteristic property of the sample to provide an indication of the presence and/or absence of one or more target considerations.

In one embodiment of the invention, the optical system can comprise at least one light source such as light emitting diodes optically coupled to at least one refractometer, typically through a window, which can be a sapphire window. The window is typically a sapphire window disposed against or as a part of a flow line containing the fluid to be characterized. The refractometer uses the light reflected of the window to qualitatively identify the fluid phase in the flowline. At the selected angle of incidence, the reflection coefficient is much larger when gas is in contact with the window than when oil or water contacts it. In further embodiments, the optical system can further comprise a second light source and detector assembly that determines the absorption characteristics of a fluid. One or more broadband light sources such as a high-temperature halogen tungsten lamp can transmit a broad spectrum light through the fluid. The distribution of transmitted light is measured throughout the visible and near-infrared spectra. A plurality of channels can be used to selectively determine, observe or quantify the light for a plurality of wavelength ranges of the spectra. The measurement from each of the channels provides a characterization of the relative amount of the corresponding component in the sample.

Figure 4:
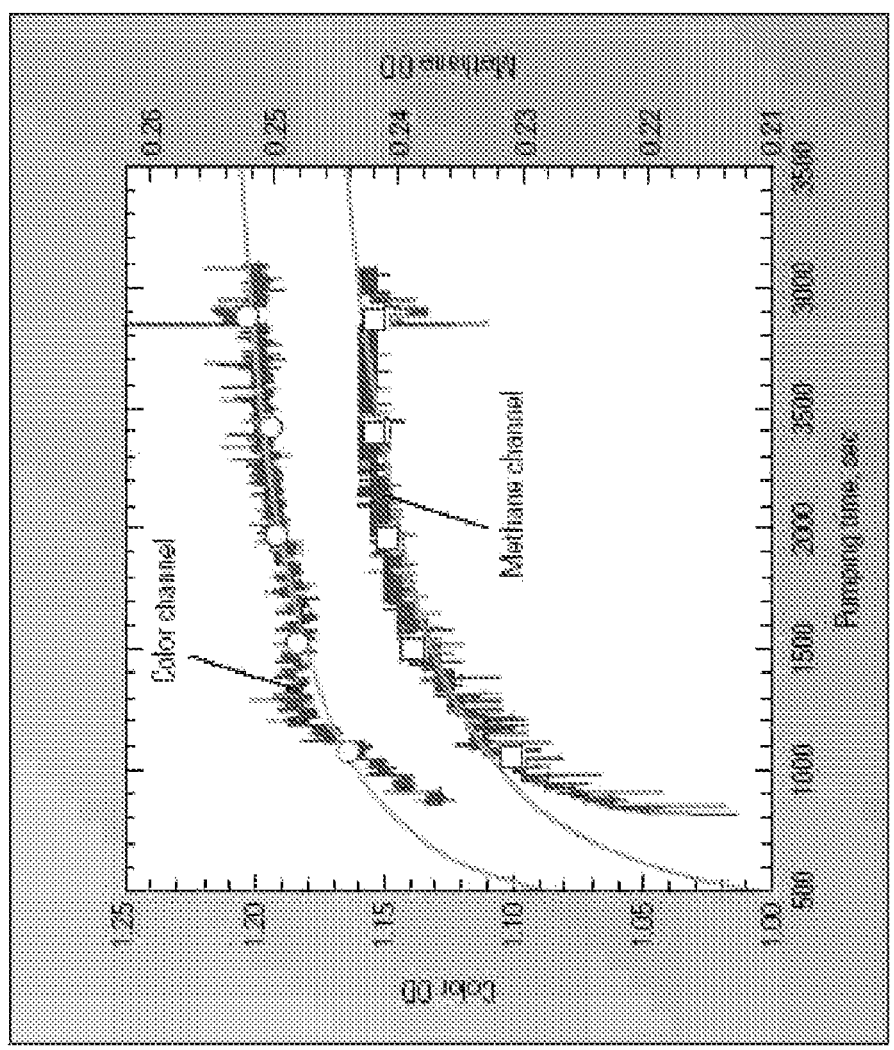
FIG. 4 is a chart showing the contamination prediction of an oil sample using a Live Fluid Analyzer on a formation tester.

Further, discriminating particulate contaminants, such as mud solids, can be performed because the presence of such is typically manifested as noise in the OD measurement. For example, FIG. 4 shows a chart which can be used in optical methods to track contamination in a formation fluid from an oil-based mud (OBM) filtrate. A Live Fluid Analyzer or LFA™, from Schlumberger, as substantially described by Andrews et al., Oilfield Review, pp. 24-43, Autumn 2001, can be used in real-time. The OBM filtrate is colorless and also has no dissolved methane. As pumping continues and contamination drops in the sampled fluid, the fraction of formation fluid in the sample increases. This is manifested as an increase in the optical density in the color and methane wavelength channels, which increases and then stabilizes as contamination levels off. In the sampling example shown in the figure, the color channel data predicted about 4.9% of contamination and the methane channel data predicted about 6.2% contamination. The 5.5% average agreed with a 4.3% contamination from determined GC analysis of the collected sample in the laboratory.

Figure 5:
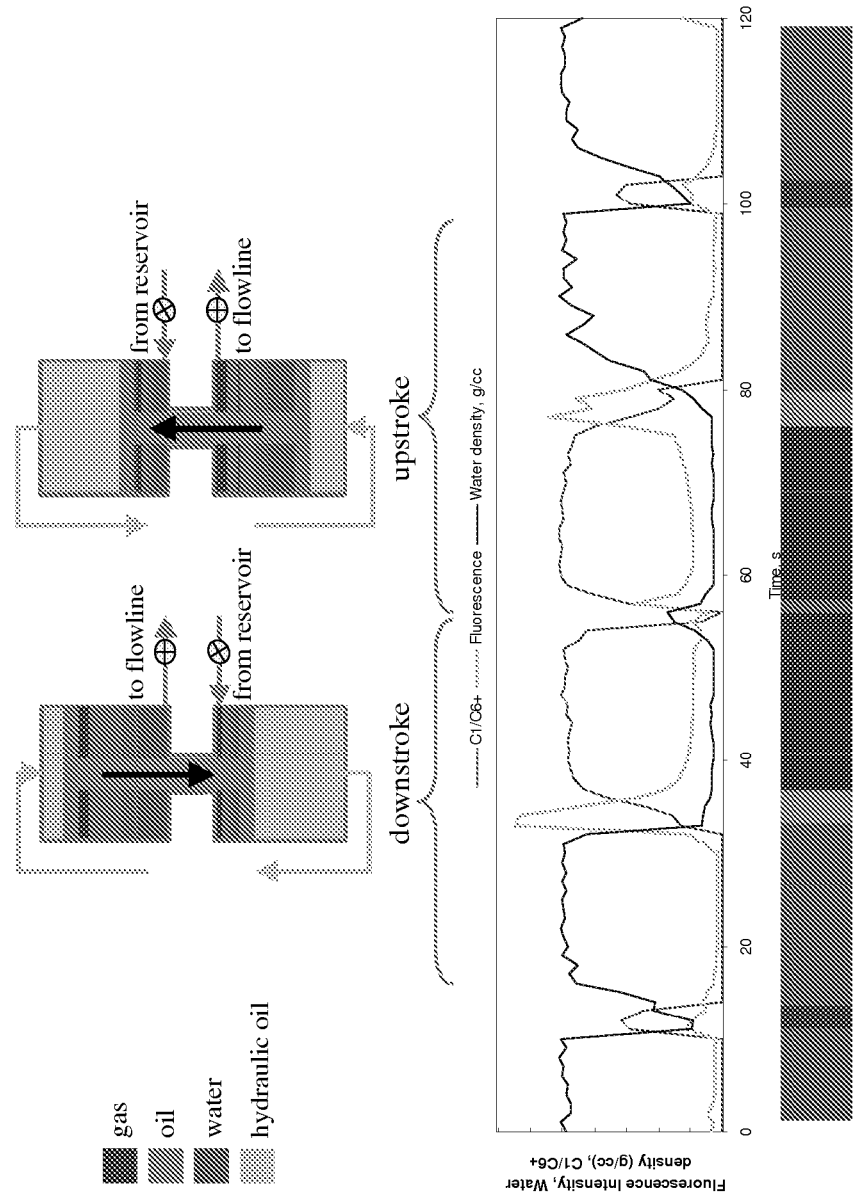
FIG. 5 is a chart illustrating detecting multiple phases downstream of a pumpout module using a Composition Fluid Analyzer on a formation tester.

FIG. 5 (based upon data contained in Betancourt et al., SPE 87011, SPE Asia Pacific Conference, Kuala Lamour, Malaysia, March 2004)) shows optical measurements can be made with a composition fluid analyzer positioned downstream of a pumpout module in a formation tester tool. The pump out module causes gravity segregation of the gas, oil and water phases. The optical signals from fluorescence and absorption measurements map the oil-water-gas slugs as they flow past the optical sensor in the flowline. This prior primary characterization is potentially important in avoiding water sampling and selecting representative single-phase oil and gas samples for a secondary analysis using a chromatography train.

Thus, in some aspects of the invention, the efficiency of downhole chromatographic systems and techniques can be enhanced or improved by facilitating real-time evaluation on when to sample. For example, optically based primary characterization subsystems can ensure that gas chromatographic (GC) analysis is performed only when no water is present. In many mixed hydrocarbon-water flows, the pump module acts as a downhole separator and produces slugs of water and hydrocarbon. Using primary characterization tools as a guide can be used in sampling to catch a hydrocarbon slug. This would ensure a relevant measurement and prevent damage to water sensitive columns. Similar separations can occur when there is oil/gas flow. Thus the optically-based primary systems, for example, may be used to guide sample timing to retrieve an oil sample and then in the next run a gas sample.

The chromatographic trains of the invention typically include one or more sampler/injectors, one or more columns, and one or more detectors fluidly connected to provide a relative characterization of the eluent from the one or more columns. Typically, the detectors can be, for example, flame ionization detectors or thermal conductive detectors and the columns contain a stationary phase, for example, a gel or other suitable material that exhibits an affinity for one or more components of the analyte.

In one or more preferable embodiments, the optically-based systems can rapidly and/or continuously facilitate determining optimum GC sampling cycles based on contamination. For example, a sample would typically be retrieved only when the contamination is low enough that the sample analysis is useful. While the GC can be used to track contamination, it would be preferable to reduce the number of GC analyses because GC analysis typically takes longer than, for example, optically-based analytical techniques. In contrast, optically-based primary analysis can continuously monitor the contamination and trigger additional characterization when contamination is considered low enough that, for example, a GC analysis of the sample is relevant. Avoiding or reducing the dependence of chromatographic characterization for contamination tracking can reduce the time the tool spends at a fluid sampling station as the GC analysis typically takes longer than an in situ optical analysis in the wellbore. This reduces the risk of tool sticking. Additional advantages of selective sampling or categorizing contamination prior to chromatographic characterization can reduce the consumption of carrier phase. Thus, in some embodiments, smaller overall systems can be utilized because of a reduced operating requirement to perform similar quantitative and/or qualitative analysis. Further the column degradation is minimized so that more relevant representative sample analysis can be performed before the column needs to be reconditioned.

Methane and carbon dioxide often can co-elute. Optically characterizing the methane component mole fraction allows for the determination of the relative amount of carbon dioxide by, for example, compensating the measured methane contribution from a combined methane and carbon dioxide measured determined by chromatography. Thus, some embodiments of the invention can avoid chromatographic methods that are typically utilized to separate methane and carbon dioxide, which are methods that typically have a longer analysis time. Thus, some aspects of the invention pertain to combining the chromatographic analysis with optical analytical system for better quantification and interpretation. Optical analysis with the CFA™ gives C1, C2-C5 and C6+ and these outputs may be used to check for consistency with GC measurements. If there are significant differences, it is detected in real-time and allows one the opportunity to repeat the measurement.

Yet another feature of the invention can pertain to utilizing primary fluid property information to improve or even optimize chromatographic analysis. For example, the characterization system or tool can comprise one or more stored analytical protocols comprising, for example, temperature programs, carrier gas flow rates, and/or pressure schedules. The various protocols can be used, depending on the type of the hydrocarbon, e.g., dry gas, light oil, heavy oil, etc., to select an optimum and/or a preferred analytical protocol, typically in real-time, to improve resolution and provide fast analysis.

In some embodiments of the invention, the density and/or viscosity of the analyte can be determined at downhole conditions, for example using vibrating sensors, such as those disclosed in WO2002077613 and WO2006094694, to provide an initial characterization. The viscosity information can be used to get qualitative information on hydrocarbon type, light or heavy. The density information can be used to quantify the chromatogram more robustly.

As explained earlier, because of incomplete vaporization in sample/injection unit or strong adsorption on stationary phase etc., not all of the sample components may elute into the chromatogram. Current lab methods use internal standards, such as described in ASTM D5307-97 and D5442-93, to determine this missing mass in the chromatogram. This fraction is termed the plus fraction and together with the mass fractions of all the other components, can provide the total fluid composition. This information can then be used to estimate the relationship between pressure, volume and temperature with the EOS. Characteristic constants of the equation of state are typically tuned using an accurate and detailed composition and measured fluid properties such as bubble point, dew point, phase miscibility with other components, compressibility, density etc. (see Ahmed et al SPE 15673). Under downhole conditions, it is difficult to make quantitative mixtures with internal standards and fluid sample. Generally the chromatographic sampler would allow for extracting exact volumes of the fluid at the downhole pressure and temperature by using for example, precision sample loops. Recent publications, such as WO2002077613 and WO2006094694, disclose vibrating devices that measure density at downhole conditions with high accuracy. Using the measured density and the volume, the total mass of the sample that is used for the chromatography analysis can be calculated. The peak areas of the eluted components in the chromatogram can be used to get the mass of each eluted component. The difference between the total eluted mass and the input mass is the missing mass. This allows determination of the mass fraction of eluted components and the plus fraction and hence the total composition of the fluid, which can then be used as input information for the EOS models.

The systems and techniques of the invention contemplate utilizing additional fluid sensors for downhole measurements such as for example NMR as disclosed in (Lo et al., SPE 77264, SPE Journal, March 2002, pg 24-34) for hydrocarbon fluid viscosity and gas-oil ratio. Resistivity sensors can be used to differentiate between water and hydrocarbon fluids. Other sensors that measure fluid phase transition properties such as bubble point, dew point, wax appearance temperature, asphaltene onset pressure could also provide information that can be integrated with downhole gas chromatography analysis to further facilitate EOS tuning downhole and also allow for real time consistency validation across all measurement sensors.

Figure 6:
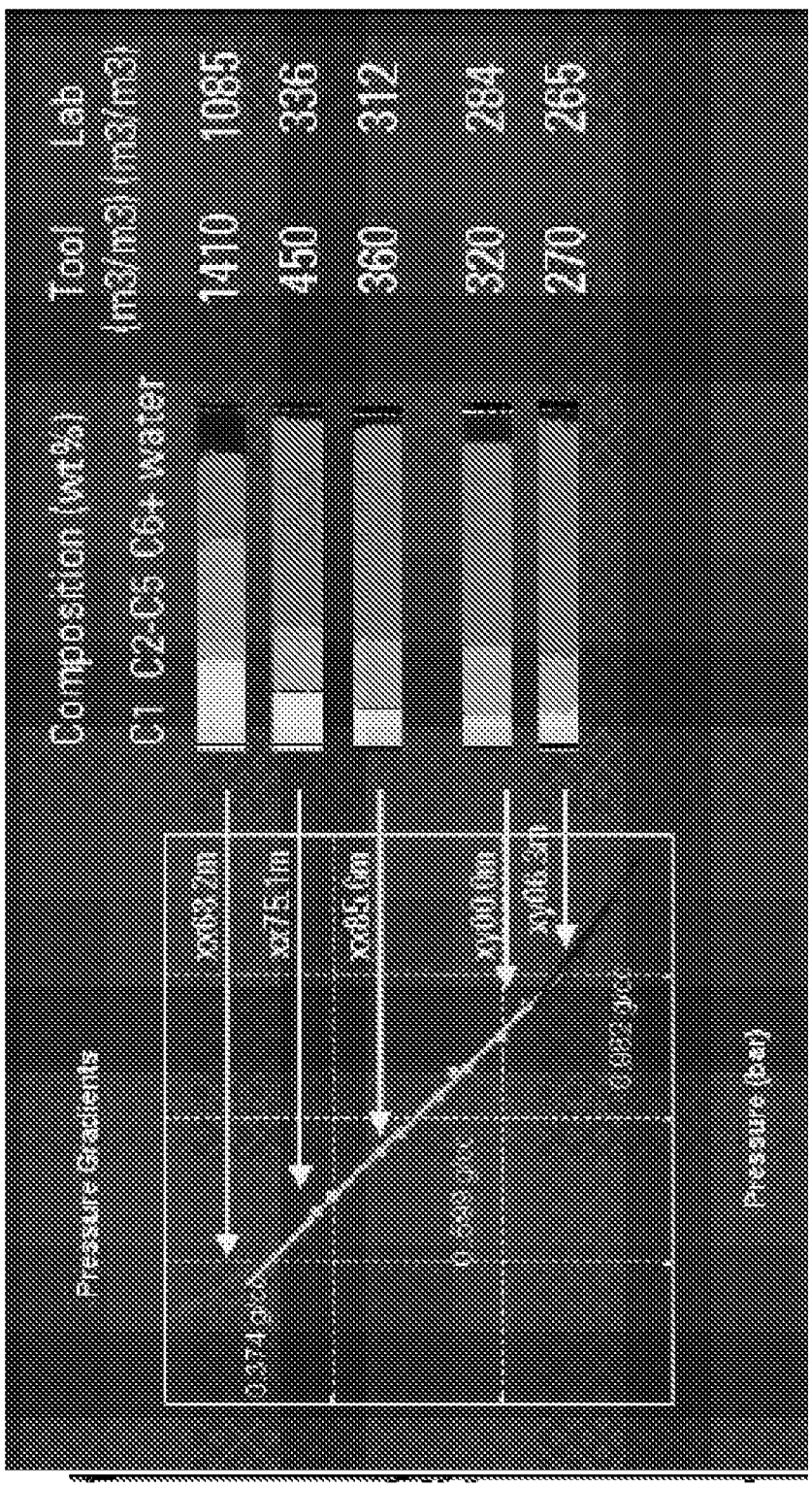
FIG. 6 is a chart showing downhole fluid analysis logs from an oil zone using a Composition Fluid Analyzer on a formation tester.

FIG. 6 shows downhole pressure and fluid analysis logs from an oil well using a composition fluid analyzer on a formation tester. These fluid analysis logs are based on data from Fujisawa et al, SPE 89704, SPE ATCE, Houston, Tex., September 2004). The pressure logs clearly indicate the presence of a gas, oil and water zone in the formation. The fluid logs at the five sampling stations show a large compositional variation in the hydrocarbons as seen in the C1, C2-C5 and C6+ fractions as well as GOR, shown as m3/m3 on the right side. The variation was confirmed by subsequent laboratory measurements. The upper station fluid (xx68.2 m) with a high GOR was interpreted to be in the gas cap region and is a retrograde gas condensate with low color and about 34 wt % of C6+. The lower station (xy06.3 m) is determined to be a heavier black oil with more aromatics and about 72 wt % as C6+. Thus if a chromatography analysis was to be performed in this well, the same system would have to analyze both gas samples at the shallow depths around xx68.2 m as well as heavier black oil samples at depths around xy06.3 m. Typical chromatography protocols start at low temperatures to provide sufficient resolution among the lighter components and then ramp up the temperature to elute the heavier components. The analysis may be followed up with a conditioning cycle and/or backflushing to remove non-eluted components. Chromatographic separation and analysis for a gas sample can be achieved in a shorter time and with lower maximum temperature to elute all components as compared to separation and analysis of heavier oils. Higher maximum temperatures through temperature ramping for the heavier oil would also mean longer cooling times before starting a subsequent analysis. It is also likely that the heavier oil would have more missing mass and would require a reconditioning cycle and/or backflushing after the analysis to remove any non-eluted components from the column. Prior knowledge from optical analysis aids in optimizing the chromatography protocols such that one could use a more rapid protocol for the gas sample if one had a priori knowledge about the hydrocarbon type. Note also that this a priori knowledge would avoid chromatography analysis stations in the water zone.

Having now described some illustrative embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto; the invention may be practiced otherwise than as specifically described.

Moreover, it should also be appreciated that the invention is directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope of the invention as embodied in the claims. Further, acts, elements, and features discussed only in connection with one embodiment are not intended to be excluded from a similar role in other embodiments.

As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An analytical system comprising:
    a primary characterization stage disposed to receive an analyte and provide an indication of at least one property of the analyte, wherein the retrieved analyte is determined as a valid analyte sample based upon the indicated at least one property; and
    a secondary characterization stage disposed to receive at least a portion of the analyte of the validated analyte sample and comprising at least one chromatographic analytical train.

2. The analytical system of claim 1, wherein the primary and secondary characterization stages are contained in a housing.

3. The analytical system of claim 1, further comprising a controller operative coupled to receive a signal from the primary characterization stage and transmit at least one control signal to the secondary characterization stage.

4. The analytical system of claim 1, wherein the primary characterization stage comprises an optically-based detector configured to provide an indication of at least one a fluid type, contaminant level, and fluid composition of at least a portion of the analyte.

5. The analytical system of claim 1, wherein an output signal is configured to energize at least one of a valve and a heater of the second characterization stage.

6. The analytical system of claim 1 wherein the analyte is a formation fluid.

7. The analytic system of claim 6, wherein said formation fluid is a multiphase fluid.

8. The analytic system of claim 7, wherein said formation fluid has a water phase.

9. The analytic system of claim 7, wherein said formation fluid has a gaseous hydrocarbon phase.

10. The analytic system of claim 7, wherein said formation fluid has a liquid hydrocarbon phase.

11. A method of characterizing an analyte comprising one or more acts of:
    providing the analyte in a first characterization stage to provide an indication of at least one first property of the analyte, wherein the analyte is determined as a valid analyte sample based upon the indicated at least one first property; and
    determining the composition of at least a portion of the analyte of the validated analyte sample in a second characterization stage based at least partially on the at least one first property.

12. The method of claim 11, further comprising an act of determining a hydrocarbon content of at least a portion of the analyte in the first characterization stage.

13. The method of claim 12, further comprising an act of transmitting a control signal to the secondary characterization stage based at least partially on the measured hydrocarbon content.

14. The method of claim 11, wherein the act of determining the composition of the at least a portion of the analyte in the second characterization stage comprises an act of chromatographically separating the components of the analyte.

15. The method of claim 14, further comprising an act of detecting the components of the chromatographically separated analyte.

16. The method of claim 14, wherein the act of characterizing the components comprises an act of generating a chromatogram representing the compositional components of the analyte.

17. The method of claim 16, further comprising an act of transmitting the chromatogram to a remote facility through a wellbore.

18. The method of claim 11, further comprising an sot of generating a first set of operating parameters of the second characterization stage based at least partially on the measured parameters from the first characterization stage.

19. The method of claim 11, wherein said analyte is a formation fluid.

20. An analytical system comprising:
a primary stage disposed to receive an analyte and provide an indication of at least one property of the analyte such that the primary stage comprises a density sensor configured to provide an indication of at least one a density, of at least a portion of the analyte; and
a secondary characterization stage disposed to receive at least a portion of the analyte
and comprising at least one chromatographic analytical train.

* * * * *